United States Patent [19]  [11] 4,039,809
Bailey  [45] Aug. 2, 1977

[54] LOWER-ENERGY NEUTRON SOURCES FOR INCREASING THE SENSITIVITY OF NUCLEAR GAGES FOR MEASURING THE WATER CONTENT OF BULK MATERIALS

[76] Inventor: Sylvia M. Bailey, 6908 Strathmore St., Chevy Chase, Md. 20015

[21] Appl. No.: 609,629

[22] Filed: Sept. 2, 1975

[51] Int. Cl.² .......................... G01T 3/00; G21G 4/02
[52] U.S. Cl. .................................. 250/390; 250/391; 250/499
[58] Field of Search ................. 250/499, 390, 391, 392

[56] References Cited

U.S. PATENT DOCUMENTS

| 3,213,280 | 10/1965 | Burley et al. | 250/391 |
| 3,492,479 | 1/1970 | Lowery et al. | 250/390 |
| 3,571,595 | 3/1971 | Silver | 250/499 |
| 3,794,843 | 2/1974 | Chen | 250/392 X |
| 3,955,087 | 5/1976 | Ashe | 250/390 X |

Primary Examiner—Archie R. Borchelt
Attorney, Agent, or Firm—A. Fred Starobin

[57] ABSTRACT

The sensitivity of a gage using a nuclear source for measuring the water content of bulk materials, such as plastic concrete, is increased by use of a lithium or fluorine neutron nuclear source.

9 Claims, 3 Drawing Figures

LOWER-ENERGY NEUTRON SOURCES FOR INCREASING THE SENSITIVITY OF NUCLEAR GAGES FOR MEASURING THE WATER CONTENT OF BULK MATERIALS

BACKGROUND OF THE INVENTION

The invention pertains to means for determining the water content of bulk materials and more particularly the use of a neutron source increasing the sensitivity of a nuclear gage in the measurement of water content of bulk material such as for example the water content of plastic concrete.

Methods are needed for measuring the amount of constituent materials, such as cement and water, in freshly mixed concrete in order to predict the final quality of the hardened concrete. At the present time, the quality control of concrete ordinarily is exercised prior to placement by inspectors who oversee the weighing-in and mixing of the cement, aggregates, admixtures, and water at batching sites. In addition, the quality of the end-product concrete is established by tests on cured specimens such as strength cylinders days and weeks after placement. Post-placement tests on cylinders which indicate strengths below specification minimums have the disadvantage that removing the hardened substandard concrete on the job site is difficult and uneconomical.

Fast neutron scattering techniques have been used for determining the water or organic content of bulk materials and especially for determining the water content in soils. The phenomenon upon which these gages are based is that high energy or fast neutrons lose a much greater fraction of their initial energy when scattered by hydrogen atoms than by atoms of any other element. The resulting low energy or thermal neutrons can then be counted by a detector which is primarily sensitive to them. This principle has been used, for example, in determining the water content of soils and in the present invention is applied to the measurement of the water content in plastic concrete.

SUMMARY OF THE INVENTION

It is an object of the present invention to increase the sensitivity of nuclear gages in their measurement of the water content or hydrogenous content of bulk materials.

It is a further more specific object of the present invention to permit rapid, simple, and accurate on-site tests for the water content of concrete still in the plastic state which would then allow acceptance or rejection of the concrete work far more economically than by use of methods and apparatus of the prior art.

Basically, the present invention involves a nuclear gage which includes a probe, shield, and scaler and means for measurement of a predetermined volume of a test sample with a radio-active source associated with the probe having the properties to allow improved sensitivity of the nuclear gage.

Furthermore, the present invention involves the use of radio-active neutron sources including sources of lithium and fluorine.

BRIEF DESCRIPTION OF THE DRAWINGS

These and other advantages and objectives of the present invention will become apparent from a detailed description thereof taken in connection with the drawings, in which.

DESCRIPTION OF THE PREFERRED EMBODIMENTS

Figure 1:
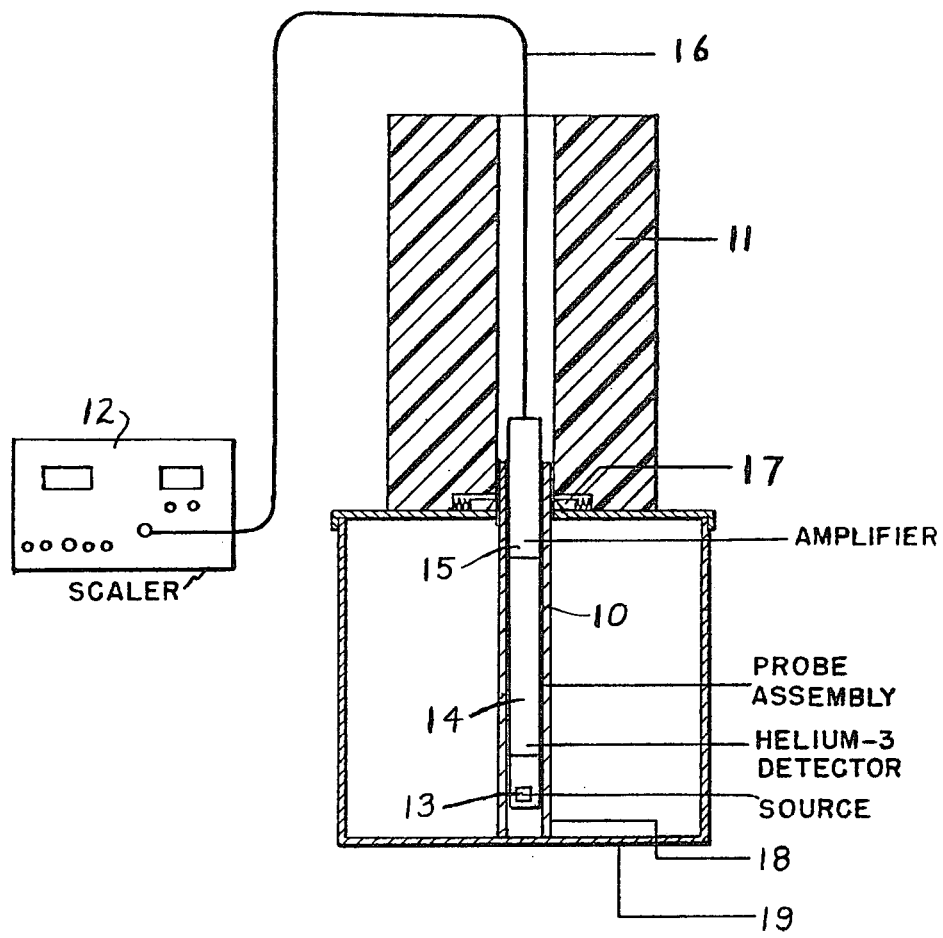
FIG. 1 is a partially sectioned diagrammatic illustration of the apparatus for measuring the water content of bulk granular material such as freshly mixed concrete with a neutron nuclear gage.

Referring first to FIG. 1, there is shown an example of the apparatus which could be used with a nuclear source further discussed below for measuring the water content of bulk material such as freshly mixed concrete.

A nuclear gage in general similar in most aspects to that shown in FIG. 1 has been described by H. A. Lepper, Jr. and R. B. Rodgers in their article entitled "Nuclear Methods for Determining the Water Content and Unit Weight of Fresh Concrete" in the *Journal of Materials* JMLSA, Vol. 6, No. 4, Dec. 1971, pp. 826–841. Their gage consisted basically of three main parts, a probe assembly 10, a shield 11 of polyethylene and a scaler 12 which could be placed on a nearby bench. Probe assembly 10 is a closed metal tube containing radioactive neutron source 13, a slow neutron detector 14 such as a helium-3 detector, and an amplifier 15 which amplifies the electronic pulse created by a slow neutron passing through the detector 14. Probe assembly 10 is connected electronically through cable 16 to scaler 12 which is used to register and count the pulses sent to it from probe assembly 10. Polyethylene shield 11 is used to house probe assembly 10 when it is not in use because of its radiation characteristics. When a sample is to be tested, probe assembly 10 is lowered past spring locks 17 shown in their retracted position, into stainless steel access tube 18 which is centered in sample holder bucket 19, and readings are obtained from scaler 12 after proper preparation of each sample of plastic concrete or other bulk material.

Specifically in the measurements taken and discussed herein, the apparatus included a Measurement Laboratories Model 401 helium-3 detector with self-contained preamplifier used with a Troxler 2601 portable scaler.

Figure 2:
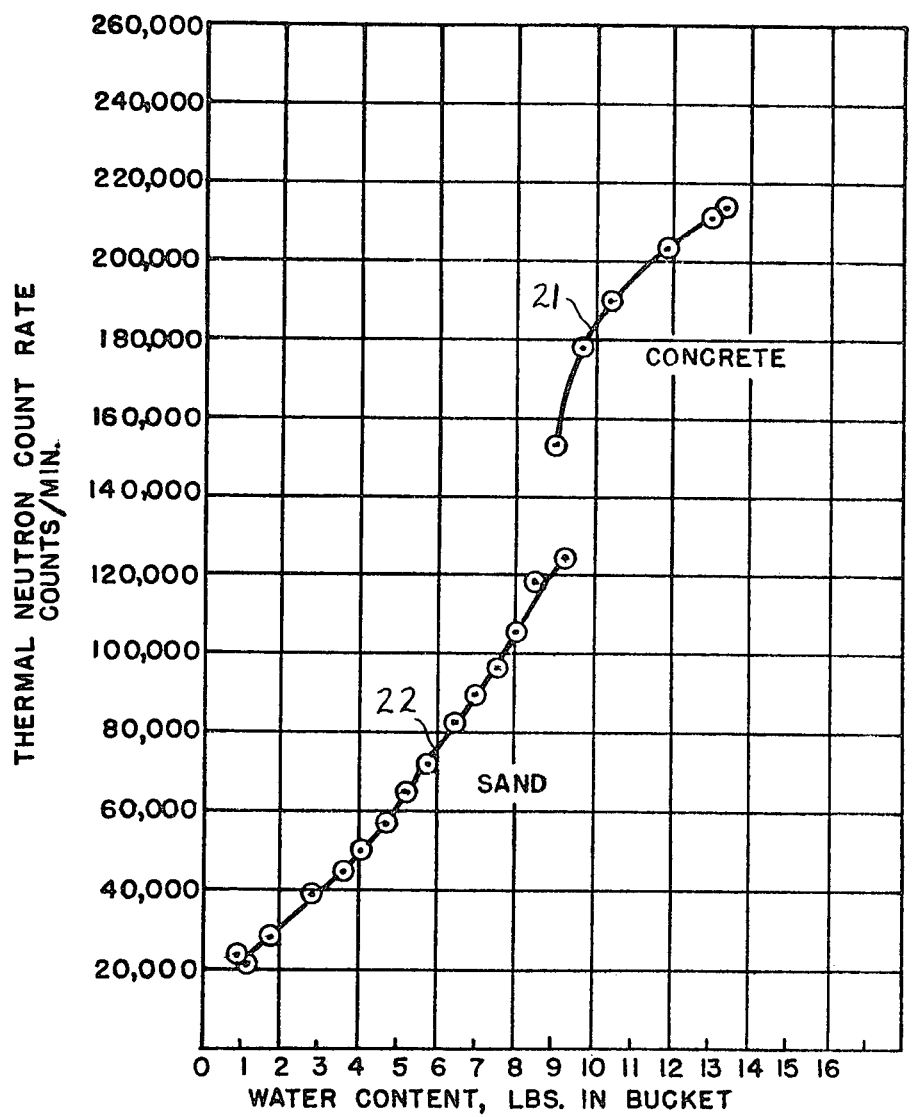
FIG. 2 is a graph of experimental results obtained for gage sensitivity comparing two different types of test samples.

The bulk materials used in obtaining the measurements illustrated in the graph of FIG. 2 were freshly mixed concrete for line 21 and moist sand for line 22.

For each bulk material, the same standard procedures were used for preparing batches and in compacting and leveling off each sample for measurement. Measurements were made on four concrete samples prepared from each batch of concrete mixed. Siliceous sand and gravel were used in making the concrete batches.

Fifteen sand samples of varying moisture content were prepared by successively mixing a sand batch, making a gage measurement, adding an increment of water, remixing, and making a gage measurement on the newly prepared sample. The results for sand using the 300 mCi Am-Be source are compared with those for plastic concrete in FIG. 2 where neutron count rate corrected for the background count for the empty bucket is plotted versus water content. The shape of the curve for moist sand is different from that for freshly mixed concrete. The sensitivity and count rate are seen to vary with both water content and kind of material.

Standard counts, with the probe assembly 10 in its shield 11, were taken at the beginning and end of each period of work during the measurements.

Figure 3:
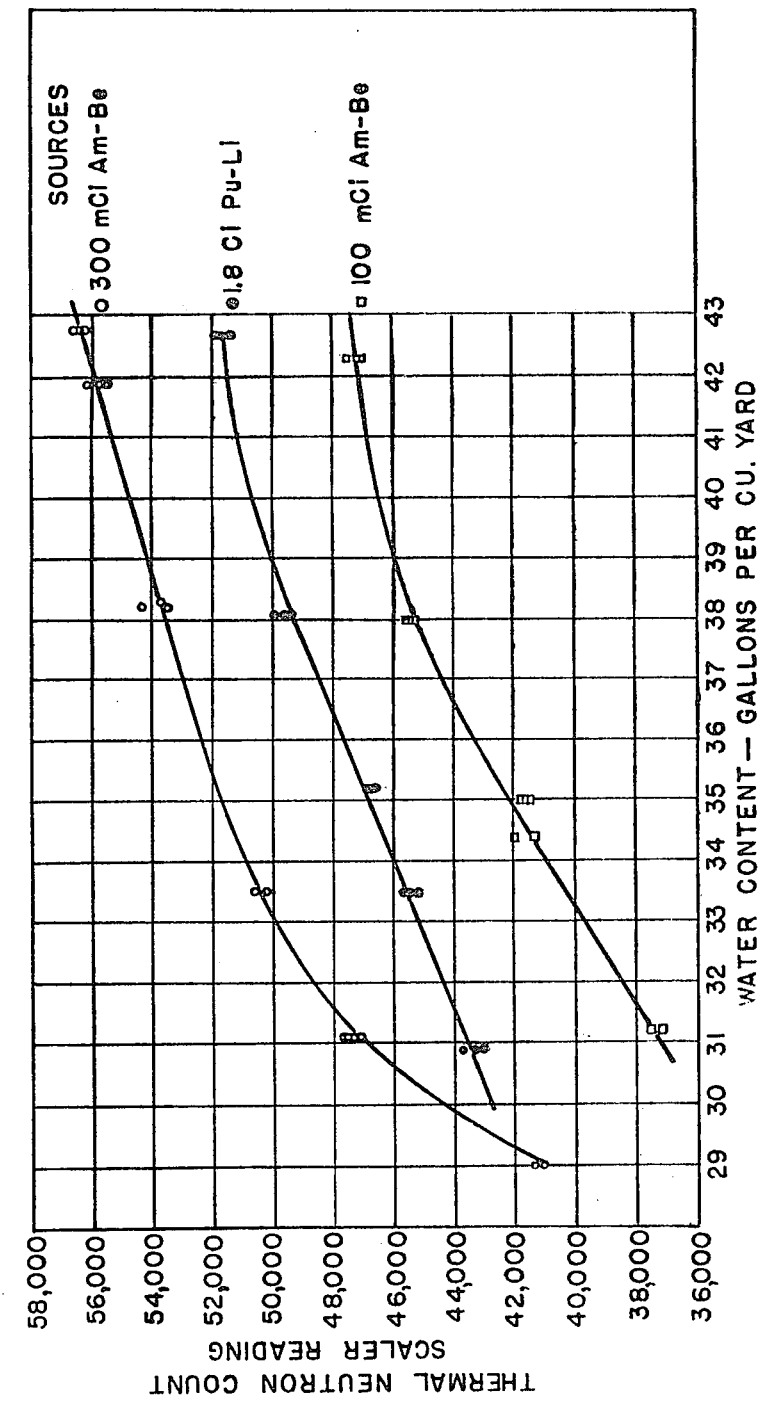
FIG. 3 is a graph of experimental results obtained for gage sensitivity comparing different neutron sources.

FIG. 3 illustrated measurements of gage sensitivity in a graph from measurements taken with three different sources.

Two radioactive neutron sources 13 of americium-beryllium from General Nuclear were used in the gage with freshly mixed concrete in bucket 19. One had a strength of 300 mCi, and the other was 100 mCi with a neutron flux intensity of $(2.08) \times 10^5$ neutrons/sec. A plot of thermal neutron count versus water content in shown in FIG. 3 for each source. These results show that gage sensitivity is little changed by changes in the intensity of the neutron flux from the source. The gage sensitivity, which is the percent change in count rate per one percent change in water content, is about (0.5% change in count rate)/(1% change in water content)

This sensitivity is at the lower end of the range obtainable with commercially-available soil moisture gages. When the bucket 19 containing freshly mixed concrete was removed from the concrete floor and placed on a wood stool, the count rate decreased by 14%. When wood blocks or concrete cylinders were placed around the bucket 19, the count rate increased by about 2%.

In order to improve the gage sensitivity, a 1.8 curie neutron source of Pu-238 and lithium was used. This source in Monsanto Model No. 2723A. The neutron flux of this lithium source is $1.17 \times 10^5$ neutrons/sec which is about one-half the neutron intensity of the 100 mCi Am-Be source. The energy spectrum of this lithium source is close to that of the Po-$\alpha$-Li$^7$ source given by *Reactor Physics Constants* by Argonne National Laboratory, 2nd Edition, ANL-5800 (July 1963), where the peak energy is shown as about 0.25 Mev. The beryllium sources have a peak energy of about 4.5 Mev. As shown in FIG. 3, the sensitivity curve for the lithium source is generally similar to that for the beryllium sources. In FIG. 3, the neutron count rate was not corrected for the relatively small background count in the empty bucket.

For the particular case at hand regarding a bulk material such as plastic concrete the use of a lithium source instead of a beryllium source is to increase the sensitivity by increasing the fraction of neutrons emitted by the source which are moderated by the water content and detected by detector 14. If the fraction of neutrons detected by the detector is greater, there is a greater possibility of increasing the sensitivity to water content. The means of increasing the fraction of neutrons moderated and entering the detector 14 is to use a source 13 which emits neutrons of a lower energy. These lower-energy neutrons are expected to become thermalized at a shorter distance from the source-detector region. The reasons for such expectations are as follows:

1. The slowing-down power of neutron moderators is greater for lower-energy rather than higher-energy fast neutrons. The effectiveness of nuclei as neutron moderators can be considered to be expresed by the microscopic slowing-down power which is given as $\xi\sigma_s$ where $\sigma_s$ is the microscopic scattering cross section and $\xi = \ln E_1/E_2$ with $E_1$ and $E_2$ as the initial and final energies respectively.

The energy spectrum of $(a, n)$ sources is divided into two groups: 10 Mev to 0.183 Mev and 0.183 Mev to 1.44 ev. The $\xi\sigma_s$ values for the two energy groups are calculated and shown in a table in "Neutron Moisture Gauges" LAEC Technical Reports Series No. 112 (1970). For hydrogen moderator, the $\xi\sigma_s$ values are 2.761 and 19.20 for the higher and lower energy groups, respectively. This shows that hydrogen is seven times more effective as a moderator for the lower-energy group than for the higher-energy group.

2. Materials impede the movement of neutrons away from the source-detector region to a greater extent for the lower-energy fast neutrons than for the higher-energy group. The microscopic transport cross-section, $\sigma_{tr}$, is a measure of this impeding of motion away from the source-detector and is calculated for the two above-mentioned energy groups of fast neutrons and is shown in the above table in "Neutron Moisture Gauges". $\sigma_{tr}$ is 3.74 times larger for hydrogen and 4.1 times larger for iron for the lower-energy group than for the higher-energy group. Elements of higher atomic number are more effective in keeping the scattered neutrons in the vicinity of the source 13 than elements of lower atomic number.

The practical proof of this is the observed increase in nuclear moisture gage readings on soil with increasing soil density at a given hydrogen content.

3. The scattering mean free path in water decreases from 6.5 cm to 1.25 cm when the neutron energy decreases from 5 Mev to 0.22 Mev.

4. Experimental work by A. M. Munn and B. Pontecorvo reported in "Spatial Distribution of Neutrons in Hydrogenous Media Containing Bismuth, Lead and Iron" *Canadian Journal of Research* A25, 157 (1947) on two energy groups of fast neutrons confirm that the mean square distance from the source of the slowed-down neutrons is less for lower-energy than higher-energy fast neutrons.

It takes four collisions on the average to decrease the neutron energy from 4 Mev to 0.25 Mev. About eighteen collisions are required to reduce the neutron energy from above 2.5 Mev to near thermal energy.

While the count rate for the 100 mCi Am-Be source is roughly one-third that of the 300 mCi Am-Be source, the count rate for the lithium source is about twice as great as would be expected when its neutron flux is compared with that for the 100 mCi Am-Be source. This confirms that using a neutron source of lower-energy increases the fraction of neutrons moderated and counted by the detector. However, the failure of the use of the lithium source to improve significantly the sensitivity of the nuclear gage is considered to be due to the approach of a saturation effect at this lower neutron energy. In other words, the water content of the bulk material may be so high that the hydrogen nuclei moderate nearly all of the lower-energy neutrons at such a similar and close distance from the detector that about the same fraction of neutrons is counted throughout the range of the water content variation. This is consistent with the observed smaller percent change in count rate over the total range of water content variation in the case of the lithium source than in the case of the weaker beryllium source with the more comparable neutron flux. For a lower range of moisture content, You Min Chen as inventor in U.S. Pat. No. 3,748,473, issued July 24, 1973, reported increasing the sensitivity of a neutron scattering gage for bulk materials by the use of a lithium source; however, Chen used a transmission configuration in which the sample is placed between the source and the detector. Chen noted that a saturation effect occurs at high moisture content when a lower-energy neutron source is used. In the present invention, a higher-energy neutron source is used to measure a higher water content in a material without a saturation effect.

In the back-scattering gage configuration used in this study, the gage sensitivity is determined by the combined effects of the hydrogen content and the transport properties of all the elements in the bulk material. This is confirmed by the two different sensitivity curves for sand and plastic concrete shown in FIG. 2.

With a different kind of material containing a sufficiently low hydrogenous content, it is possible with the use of a lithium source to improve significantly the sensitivity of a neutron nuclear gage with the configuration of a probe assembly 10 lowered into a sample bucket 19 as described in FIG. 1. Such a gage for measuring hydrogen content is useful in the quality control of a possible variety of bulk material containing hydrogenous substances.

Since the average neutron energy reported by J. B. Marion and J. L. Fowler in "Fast Neutron Physics", Part 1, Interscience Publishers, Inc., New York, 1960, for the α-fluorine source is 1.5 Mev with a range of 0 to 3 Mev shown on page 710 in FIGS. 9–42 of Reactor Physics Constants by Argonne National Laboratory, 2nd Edition, ANL-5800 (July 1963), previously cited, which is intermediate between the energies of the lithium and beryllium sources, the neutrons from a fluorine source are considered to have a high enough energy to prevent this saturation effect. Therefore, a fluorine source tends to increase the sensitivity of nuclear gage measurements of water content of freshly mixed concrete in this back-scattering configuration.

It will be obvious to those skilled in the art that various changes may be made without departing from the scope of the invention and the invention is not to be considered limited to what is shown in the drawings and described in the specification.

What is claimed is:

1. A gage for measuring the water content or hydrogenous content of plastic concrete or materials of similar characteristics comprising means for holding a predetermined amount of plastic concrete or materials of similar characteristics of which the water content is to be measured, a nuclear source located adjacent said holding means, detector means for detecting low energy neutrons located adjacent said holding means, means to register output from said detector means connected electrically to said detector means, said nuclear source being a radioactive neutron source of intermediate fast neutron energy in the range from 1.0 to 2.5 Mev with an average of about 1.5 Mev.

2. The gage of claim 1, wherein said detector means is located adjacent said nuclear source positioned to measure back-scatter effect.

3. The gage of claim 1, wherein said nuclear source is a fluorine source.

4. The gage of claim 3, wherein said nuclear source is an α-fluorine source.

5. The gage of claim 3, wherein said detector means is located adjacent said nuclear source positioned to measure back-scatter effect.

6. The gage of claim 5, wherein said holding means holds a predetermined measured amount of concrete in a plastic state of which the water content is to be measured, said nuclear source and said detector means being adjacent each other in a substantially centrally located position in said holding means.

7. A method of measuring the water content or hydrogenous content of plastic concrete or materials of similar characteristics comprising the steps of putting a measured sample of plastic concrete or materials of similar characteristics into a container, inserting a probe having a radioactive neutron source of intermediate fast neutron energy in the range from 1.0 to 2.5 Mev with an average of about 1.5 Mev and a detector for detecting low energy neutrons, measuring the moisture content of the material.

8. The method of claim 7, further characterized by said neutron source being a fluorine source.

9. The method of claim 8, further characterized by said neutron source being an α-fluorine source.

* * * * *